United States Patent [19]

Riquier

[11] Patent Number: 5,382,227
[45] Date of Patent: Jan. 17, 1995

[54] APPARATUS AND METHOD FOR SETTING THE LEVEL OF A LIQUID IN A CHAMBER OF AN EXTRACORPOREAL BLOOD CIRCUIT

[75] Inventor: Jean-Claude Riquier, Rilleux, France

[73] Assignee: Hospal Industrie, Meyzieu Cedex, France

[21] Appl. No.: 831,532

[22] Filed: Feb. 5, 1992

[30] Foreign Application Priority Data

Feb. 6, 1991 [FR] France ................ 91 01564

[51] Int. Cl.⁶ ............................................. A61M 37/00
[52] U.S. Cl. ............................................. 604/4; 604/5; 128/DIG. 13
[58] Field of Search .............. 604/4, 5, 6, 8, 9, 65, 604/67, 23, 30; 128/DIG. 13, DIG. 14; 210/646

[56] References Cited

U.S. PATENT DOCUMENTS

| | | |
|---|---|---|
| 3,756,234 | 9/1973 | Kopp . |
| 3,830,234 | 8/1974 | Kopp ................................ 604/30 |
| 3,964,479 | 6/1976 | Boag et al. . |
| 4,231,366 | 11/1980 | Schael ........................ 128/DIG. 13 |
| 4,411,792 | 10/1983 | Babb ................................. 604/30 |
| 4,486,189 | 12/1984 | Troutner et al. ................... 604/5 |
| 4,490,135 | 12/1984 | Troutner . |
| 4,540,399 | 9/1985 | Litzie et al. ....................... 604/4 |
| 4,596,550 | 6/1986 | Troutner ........................... 604/5 |
| 4,613,325 | 9/1986 | Abrams .......................... 604/246 |
| 4,643,714 | 2/1987 | Brose ................................ 604/4 |
| 4,826,482 | 5/1989 | Kamen ........................... 604/246 |
| 4,828,543 | 5/1989 | Weiss et al. ....................... 604/4 |
| 4,850,998 | 7/1989 | Schoendorfer .................... 604/6 |
| 4,894,164 | 1/1990 | Polaschegg ....................... 604/5 |
| 4,995,268 | 2/1991 | Ash et al. ......................... 604/65 |
| 4,997,570 | 3/1991 | Polaschegg ..................... 210/646 |
| 5,057,226 | 10/1991 | Antwiler ........................... 604/5 |
| 5,098,373 | 3/1992 | Polaschegg ....................... 604/5 |
| 5,112,298 | 5/1992 | Prince et al. ...................... 604/4 |
| 5,120,303 | 6/1992 | Hombrouckx ..................... 604/4 |
| 5,171,212 | 12/1992 | Bush et al. ....................... 604/67 |
| 5,188,604 | 2/1993 | Orth .......................... 128/DIG. 13 |
| 5,190,522 | 3/1993 | Wojcicki et al. ................. 604/65 |
| 5,227,049 | 7/1993 | Chevallet et al. ................. 604/5 |
| 5,318,511 | 6/1994 | Riquier et al. .................... 604/4 |

FOREIGN PATENT DOCUMENTS 0265795  10/1987  European Pat. Off. ............ 604/9

Primary Examiner—Randall L. Green
Assistant Examiner—Rob Clarke
Attorney, Agent, or Firm—Finnegan, Henderson, Farabow, Garrett & Dunner

[57] ABSTRACT

The invention relates to an apparatus and a method for setting the level of a liquid in a chamber of an extracorporeal blood circuit. The chamber contains liquid in its lower portion and air in its upper portion. It is connected to a pump for causing the quantity of air to vary in the chamber. According to the invention, the chamber is provided with a level detector that transmits data to a control unit. The control unit actuates an air pump to vary the amount of air in the chamber and thereby ensures that the liquid level in the chamber is equal to a desired level.

13 Claims, 3 Drawing Sheets

APPARATUS AND METHOD FOR SETTING THE LEVEL OF A LIQUID IN A CHAMBER OF AN EXTRACORPOREAL BLOOD CIRCUIT

BACKGROUND OF THE INVENTION

1. Field of the Invention

The present invention relates to an apparatus for extracorporeal circulation of blood. More particularly, the invention is directed to an apparatus including an extracorporeal blood circuit having at least one chamber for containing liquid in its lower portion and air in its upper portion. The chamber is connected to a pump for causing the quantity of air to vary in the chamber.

2. Description of the Related Art

In the related art, similar devices are known which are particularly useful for treating blood by dialysis. U.S. Pat. No. ,4,490,135 describes an extracorporeal blood circuit having an arterial portion for conveying the blood of a patient to a haemodialyser, and a venous portion for returning the treated blood to the patient. Each of the arterial and venous portions includes a chamber with an upper portion connected to a pump, for adjusting the level of the liquid in the chamber by the addition or withdrawal of air. However, the operation of the pump is controlled manually according to the level of the liquid observed visually by the operator.

This visual monitoring represents a considerable constraint as far as the user is concerned, who is unable to monitor the liquid level a permanent basis. Indeed, in a treatment center such as a dialysis center, a single nurse is in charge of supervising several stations, and she must therefore supervise the proper operation of several machines, as well as the health conditions of the patients at the same time. However, maintaining the level of the liquid in the chamber is essential for an efficient and reliable treatment. It is, on the one hand, necessary to avoid spillovers of the blood and on the other hand, necessary to maintain a minimum level of liquid in the chamber. An undue fall in the liquid level in a chamber situated in the arterial portion could lead to air being introduced into the haemodialyser, which would greatly reduce its efficiency, while a fall in the liquid level in a venous chamber could lead to air being introduced into the patient's blood system, which could have serious consequences. It is therefore important to ensure proper monitoring and correction of the liquid level in the chambers on a permanent basis, without any constraints on the user and with a high degree of safety.

SUMMARY OF THE INVENTION

An object of the present invention is a device comprising an extracorporeal blood circuit including an arterial portion for conveying the blood of a patient to a treatment device, and a venous portion for ensuring restoration of the treated blood to the patient. The circuit includes at least one circulation pump, as well as at least one chamber for containing liquid in its lower portion and air in its upper portion. The chamber is connected to means, such as a pump, for causing the quantity of air within the chamber to vary. The chamber is provided with at least one level detector and includes means for controlling the pump in response to a signal from the level detector. With this structure it is possible to maintain the desired liquid level inside the chamber.

In a preferred embodiment of the invention, the means capable of causing the air quantity to vary inside the chamber is an air pump, and the means for controlling the pump includes means for determining a reference value for the signal coming from the level detector, the reference value corresponding to the desired level of the liquid in the chamber. Also included in the invention is means for determining a reference range encompassing the determined reference value; means for checking whether the signal coming from the level detector falls within the determined reference range; means for determining whether the action to be carried out is to add or withdraw air so that the liquid in the chamber reaches a desired level; and means for controlling the pump in order to implement a defined action if the signal coming from the level detector falls outside the reference range.

Thus, by means of the proposed device, the desired level of liquid inside the chamber can be controlled, with a minimum difference between the desired level and the level actually attained by the liquid. When the actual level comes very close to the desired level, the user of a reference range prevents any oscillation between a level that is slightly higher than the desired level and a level slightly lower than the desired level. Oscillation would otherwise occur through the alternate operation of the pump in one direction and then in the other direction.

According to the invention, the extracorporeal blood circuit is advantageously provided with a chamber situated in the arterial portion and a chamber situated in the venous portion, each chamber being fitted with at least one device capable of indicating the presence of a high liquid level, as well as the presence of a low liquid level. Thus, when the circuit is used in a double needle mode (where blood is drawn from a patient via an access different from that through which the blood is restored to the patient), the reference level for the liquid inside the chamber may be considered as an intermediate level between the high level and the low level. The detection of a low level and of a high level in each chamber makes it possible, during the single needle mode (where blood is drawn from and restored to the patient via a single access), to control the variation of the volume present in the chamber between the stage where the blood is drawn from the patient (arterial stage) and the stage where the blood is restored to the patient (venous stage).

According to a preferred embodiment, the invention includes means for making sure that the liquid level successively reaches the high level and the low level with each chamber, simultaneously.

Thus, in the single needle mode, the volume of liquid available for the treatment, which is the difference between volume of liquid present in the circuit at the end of the arterial stage and the volume of the liquid present in the circuit at the end of the venous stage, is completely controlled, allowing the efficiency of the treatment to be optimized.

An object of the present invention is also to provide a method for setting the level of a liquid in at least one chamber of an extracorporeal blood circuit, including the steps of:

a) determining that the liquid has reached a predetermined level by means of a signal coming from a level detector, b) comparing the signal coming from the level detector with a reference signal, c) determining, in accordance with the result of the comparison, the direction in which an air pump connected to the chamber is to operate—that is, whether the pump should act to add or withdraw air, and d) actuating the pump in the determined direction so that the liquid in the chamber reaches the desired level.

Using this method, the liquid level within a degassing chamber is automatically adjusted, on a continuous basis, with complete safety and without any specific need for intervention by the operator.

An object of the present invention is also to provide a method for automatically filling an extracorporeal blood circuit.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of the specification, illustrate several embodiments of the invention, and together with the description, serve to explain the principles of the invention.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

Figure 1:
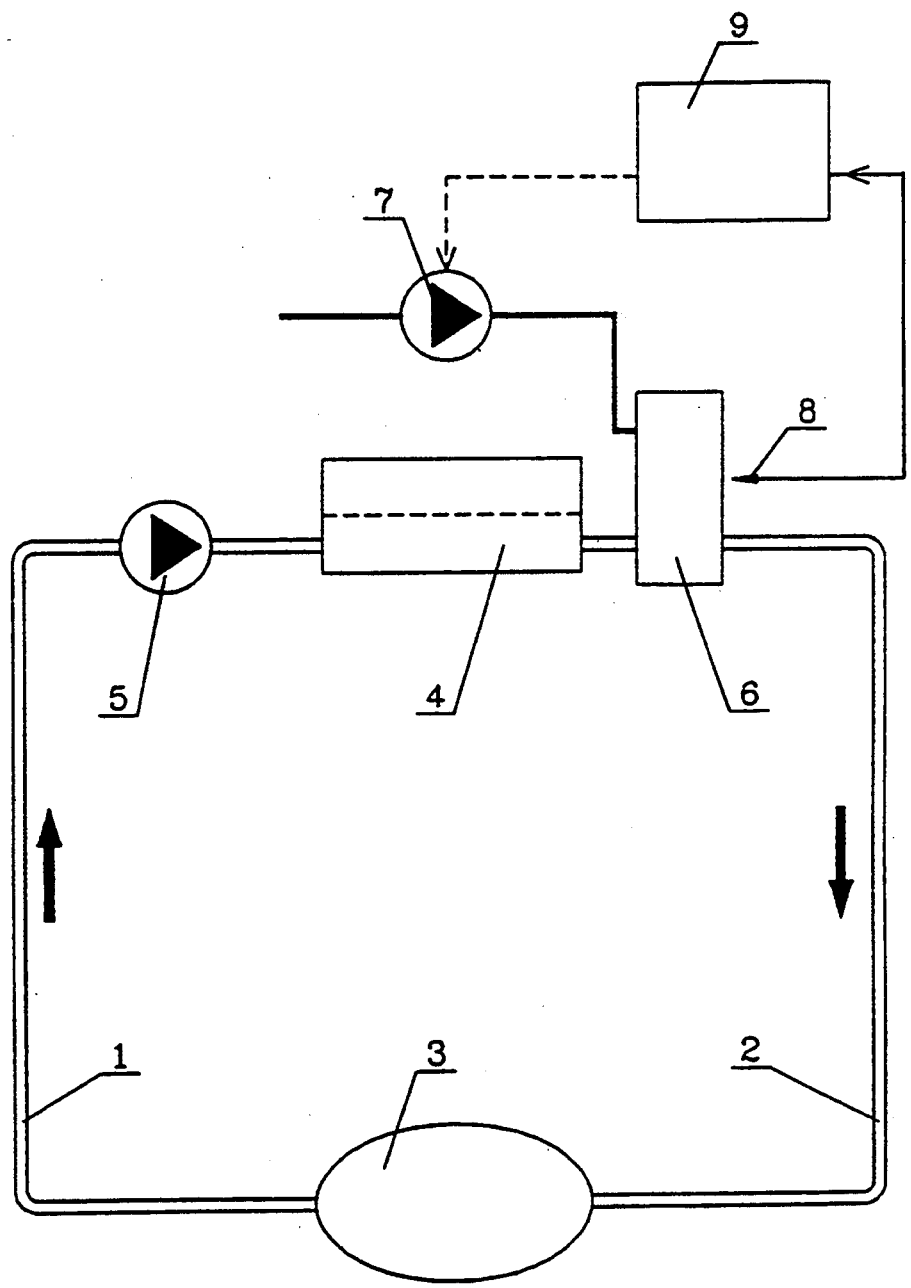
FIG. 1 is a schematic diagram of a first embodiment of the present invention, and incorporates a double needle extracorporeal blood circuit.

The extracorporeal blood circuit represented in FIG. 1 includes a conventional arterial portion 1 and a conventional venous portion 2. The arterial portion 1 conveys blood coming from a patient 3 to a treatment device 4 constituted, for example, other type of blood treatment device. For the purpose of the present description, the invention will be described in connection with a haemodialyser that is capable of treating blood by dialysis and/or by ultrafiltration. However, description of the invention in connection with a haemodialyser is not intended to be restrictive of the invention to such use.

A pump 5 ensures the circulation of the blood in the circuit as a whole. The venous portion 2 includes a degassing chamber 6, for containing liquid in a lower portion thereof, and for containing a gas, such as air, in its upper portion. The chamber 6 is connected to a pump 7 whose operation permits the quantity of gas to be modified inside the chamber. Thus, pump 7 which allows gas to be added or withdrawn from the chamber 6, makes it possible to cause the liquid level to vary within the chamber 6.

According to the invention, the degassing chamber 6 is provided with a level detector 8 for producing a signal corresponding to the liquid inside the chamber 6. Detector 8 is, for example, an optical fiber sensor for transmitting a signal proportionate to the liquid level. The signal produced by the detector 8 is transmitted to a control unit 9, such as a microprocessor, which includes means for comparing the signal produced to a reference signal corresponding to a reference level of the liquid. Control unit 9 also includes means for actuating the pump 7 when the produced signal does not correspond to the reference signal.

Thus, when the signal produced by the detector 8 corresponds to a state where the liquid level in the chamber 6 lies below the reference level, the pump 7 is actuated to withdraw air from the chamber 6 until the liquid reaches the reference level.

On the other hand, when the signal produced by the detector 8 corresponds to a state where the liquid level in the chamber is higher than the reference level, the pump 7 is actuated to add air to the chamber until the liquid level falls back again to the reference level.

To prevent the liquid level in the chamber from fluctuating on either side of the reference level by the successive operation of the pump 7 in one direction and then in the other, it is possible to compare the signal produced by the detector 8 with a reference range of values rather than a precise reference value. This range defines the limits beyond which the pump 7 is activated. In this manner, the pump 7 is only actuated when the liquid level differs from the desired level to an undue extent.

In a variation of the above-described embodiment, the level detector employed makes it possible to detect whether the liquid is present at a desired level using, for example, an optical type of detector. It is then advantageous to provide the degassing chamber 6 with a second level detector. The control unit 9 actuates the pump 7 to maintain the liquid level in the chamber between a lower limit marked by a first low level detector and an upper limit marked by a second upper level detector.

When the liquid level in the chamber reaches the low level detector, the signal produced by the detector is transmitted to the control unit 9 which actuates the operation of the pump 7 to withdraw air from the chamber. Conversely, when the liquid level in the chamber reaches the high level detector, the high level detector produces a signal transmitted to the control unit 9 which actuates the operation of the pump 7 to add air to the chamber. Thus, the liquid level is constantly maintained between two limits chosen by the positioning of the two level detectors which constitute the limits of the reference range of the desired liquid level.

Figure 2:
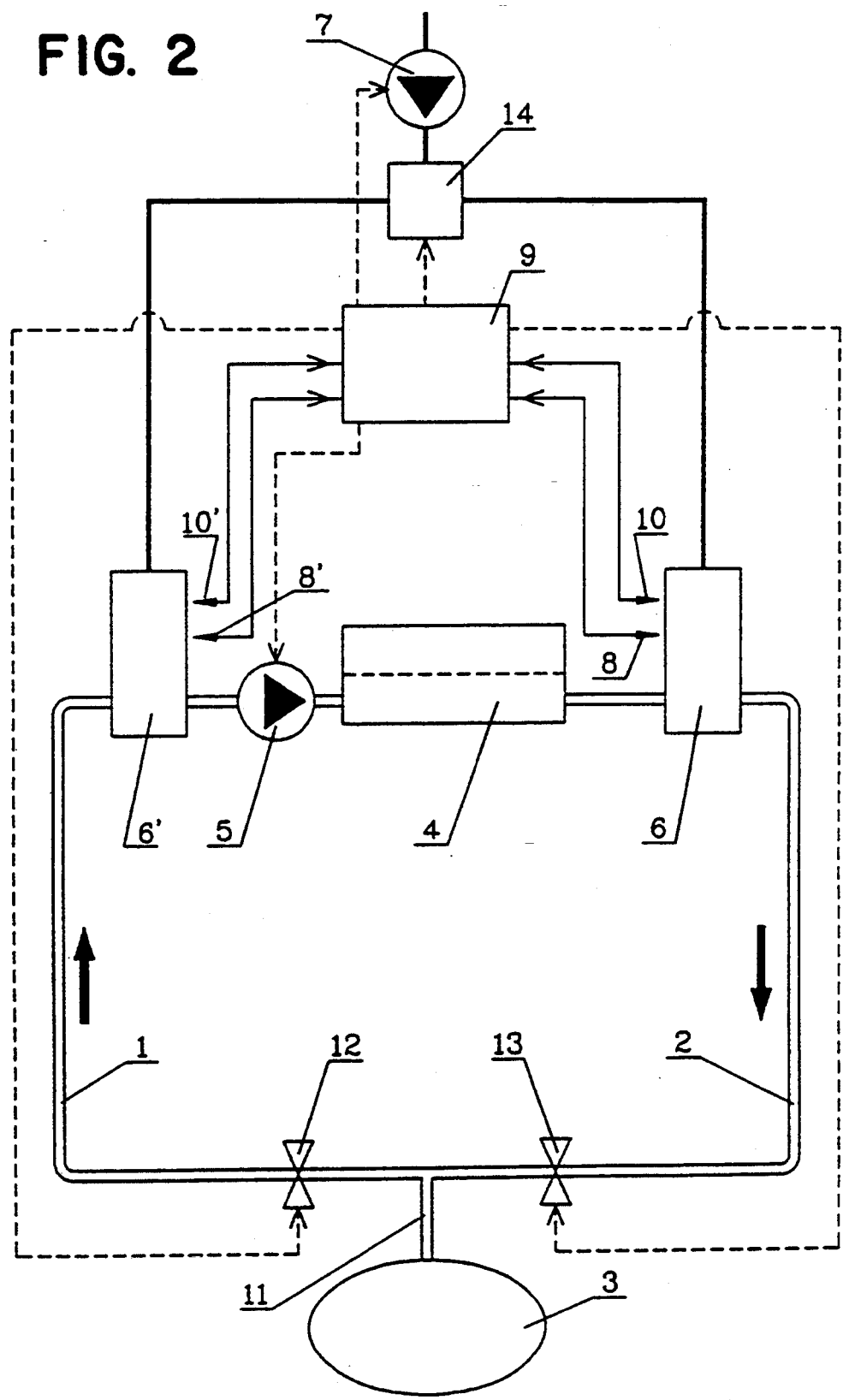
FIG. 2 is a schematic diagram of a second embodiment of the present invention, and incorporates a single needle extracorporeal blood circuit.

According to the embodiment depicted in FIG. 2, the device forming the object of the present invention is used in conjunction with a single needle extracorporeal blood circuit. In a single needle extracorporeal circuit, blood is drawn from the patient 3 and restored to the patient via single access 11, within which blood circulation alternately occurs in one direction and then in the other.

In the embodiment of FIG. 2, a clamp 12 or any other obturation device allows the inlet of the arterial portion 1 to be closed. Similarly, a clamp 13 allows the outlet of the venous portion 2 to be closed.

The arterial portion 1 includes a degassing chamber 6' whose capacity is chosen so that the chamber can be used as a buffer reservoir. The venous portion 2 also includes a degassing chamber 6 whose capacity is chosen so that the chamber can be used as a buffer reservoir. Downstream of the chamber 6', a pump 5 ensures the circulation of blood through the circuit.

According to the invention, each of the degassing chambers 6 and 6' is respectively provided with a low level detector 8 and 8' and a high level detector 10 and 10'. The detectors 8, 8', 10 and 10' are connected to a control unit 9 for controlling a pump 7 that is capable of causing a quantity of gas, such as air, to vary inside each one of the chambers. Advantageously, a single pump 7 is used which can selectively communicate with either the arterial chamber 6', or with the venous chamber 6 using, for example, a distributor 14. Distributor 14 is controlled by the control unit 9, which also controls the alternation of the opening and closing of the arterial and venous clamps 12 and 13, and the alternation rate of the arterial and venous stages.

The operation of the above described extracorporeal circuit is as follows. Blood withdrawal during the arterial stage and blood restoration during the venous stage succeed each other on an alternating basis. Thus in the arterial stage, the clamp 12 is open while the clamp 13 is closed. As the blood is withdrawn from the patient 3, the liquid level rises inside each of the degassing chambers 6 and 6'. On the other hand, in the venous stage, the clamp 12 is closed, the clamp 13 open, and the operation of the pump 5 is maintained as the blood is restored to the patient. Thus, the liquid level falls inside the chambers 6 and 6' during the restoration stage.

In order to obtain optimum efficiency from the haemodialyser 4 during the treatment time, it is important to make sure that the liquid level reaches the high level in each chamber at the end of each arterial stage and reaches the low level in each chamber at the end of each venous stage. As descried in the example below, the device of the present invention is particularly well suited to effect this control.

For the purposes of the example descried below, assume that the arterial stage, which occurs when clamp 13 is closed and clamp 12 is opened, is commenced when the liquid reaches the low level detector 8' in the arterial chamber 6'. Also assume that the venous stage, which occurs when the clamp 13 is opened and the clamp 12 is closed, is commenced when the liquid reaches the high level detector 10 in the venous chamber 6. Given these assumptions, the management of the volumes inside the chamber occurs as follows.

When the liquid reaches the low level detector 8' in the arterial chamber at the end of the venous stage, the control unit 9 starts the transition to the arterial stage by closing the clamp 13 and opening the clamp 12. The control unit 9 then starts the measurement of a period t which will elapse until the liquid in the venous chamber reaches the high level detector 10, which will then start the transition to the venous stage.

This measured period t is then compared with a theoretical value th. Value th is determined by the control unit 9 according to the delivery characteristics of pump 5, the volume of the chamber between the level of the detector 8 and the level of the detector 10, and the pressure conditions inside the chamber. The value th then represents the optimum time, for a chosen operating condition, that it takes for the liquid to rise from the low level represented by the detector 8 to the high level represented by the detector 10.

When the measured value t deviates from a reference range encompassing the theoretical value th, the control unit 9 actuates the operation of the pump 7 in order to modify the air quantity present inside one or both chambers. It is possible to check the efficiency of the correction and to adjust it if necessary by carrying out another measurement in the following cycle. It is also possible to start the time measurement in the arterial chamber from the moment when the liquid reaches the high level detector 10 in the venous chamber.

Instead of using a high level detector and a low level detector in each chamber, a single level detector may also be used, for example, with optical fibers which allows the level of the liquid within the chamber to be known at any moment. In this case, it is no longer necessary to measure the period, rather, it suffices to compare the signals coming from the level detectors of each chamber at the end of the arterial stage and/or venous stage with the corresponding reference signals.

When the signals produced correspond to levels outside the predetermined reference ranges, the control unit 9 actuates the operation of the pump 7 and the distributor 14 to cause the air quantity to vary in one and/or the other of the chambers 6 and 6'.

The determination of the actuation direction of the pump 7 may be undertaken as follows. When, at the end of the arterial stage, the liquid does not reach the desired high level in a chamber, it is necessary to actuate the pump 7 to draw air into the tardy chamber. On the other hand, when the liquid does not reach the desired low level in a chamber at the end of the venous stage, the pump 7 must be actuated so as to add air to the chamber.

Figure 3:
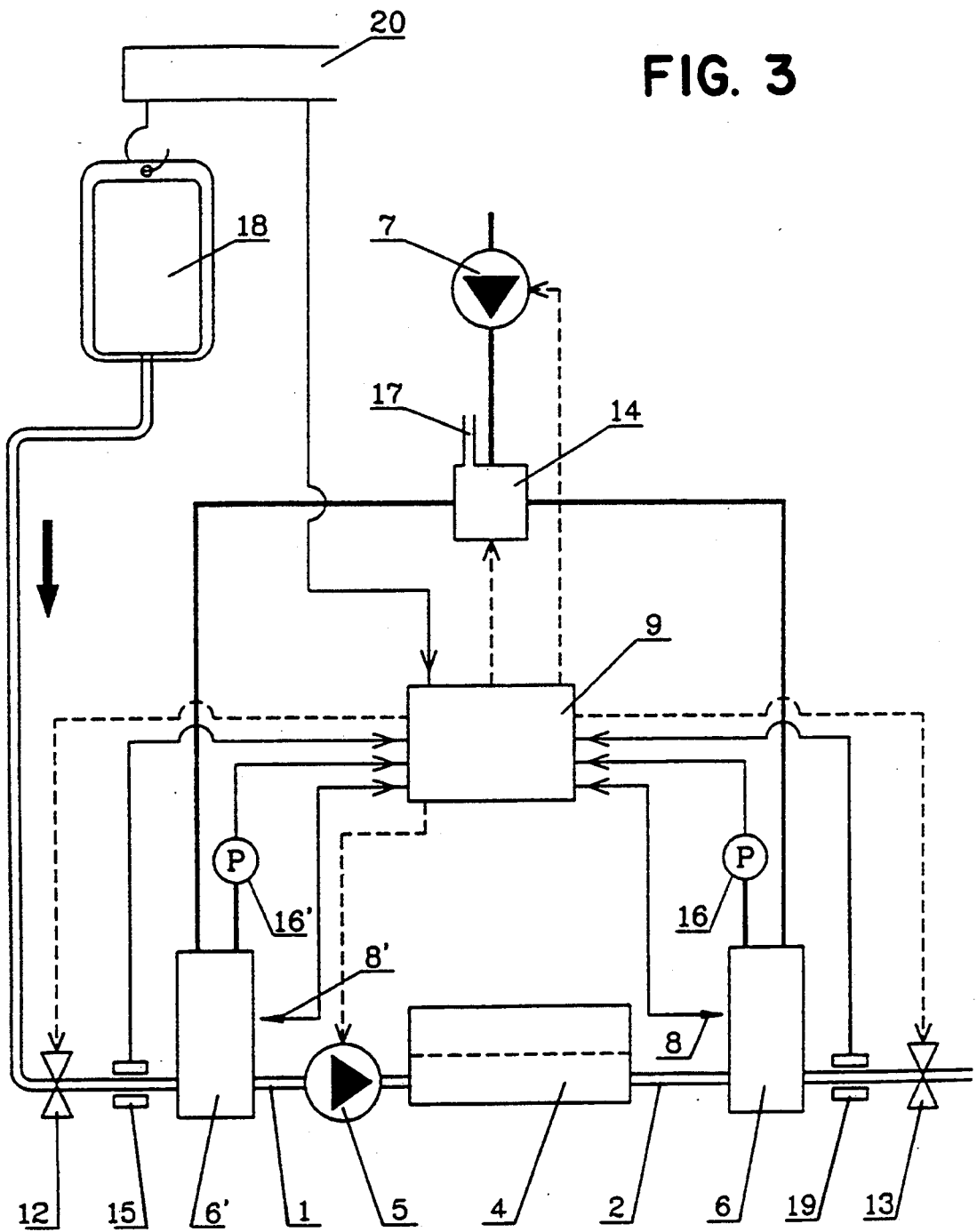
FIG. 3 is a schematic diagram of a third embodiment of the present invention, as used for automatically filling an extracorporeal blood circuit.

According to the embodiment of the invention depicted in FIG. 3, the device of the invention is particularly well suited for rinsing and automatically filling an extracorporeal blood circuit. In FIG. 3, the elements common to the figures described above bear the same reference numerals. The arterial portion 1 includes a liquid detector 15 situated ahead off and near the chamber 6'. The venous portion 2 includes a blood detector 19 situated downstream of the chamber 6 and adjacent the clamp 13. Each degassing chamber advantageously comprises a pressure transducer 16 and 16' for transmitting the values of the measured pressure to the control unit 9.

The distributor 14 allows the pump 7 to communicate with the arterial chamber 6' or the venous chamber 6. Opening 17, makes it possible to connect one or the other of the chambers 6 and 6' to the atmosphere through the distributor 14.

In order to rinse and fill the extracorporeal circuit, the arterial portion 1 is connected to a bag of a sterile physiological liquid 18 which may be suspended from a balance 20. Data from the balance 20 are transmitted to the control unit 9 which can thereby control the quantity of the rinsing liquid used. Although not shown in the figures, the venous portion 2 is connected to a receiving bag or to means for discharging the used rinsing liquid.

Liquid is circulated in the arterial portion 1 by the operation of the pumps 5 and 7 and possibly by gravity feed from the bag 18. For this purpose, the distributor 14 is adjusted so that the pump 7 communicates with the arterial chamber 6', and the clamps 12 and 13 are opened. When the physiological liquid reaches the detector 15, it sends a signal to the control unit 9 which stops pump 5. The pump 7 continues to operate up to the moment when the liquid level in the arterial chamber 6' reaches the detector 8'. When this occurs, a signal is transmitted to the control unit 9 that again commands the operation of pump 5 and sends a signal to the distributor 14 to cause the pump 7 and the venous chamber 6 to communicate with each other. The physiological liquid then flows into the haemodialyser 4 and the venous chamber 6 until it reaches the level of the detector 8 which generates a signal transmitted to the control unit 9. The control unit 9 then terminates the operation of pump 7. Pump 5 continues to ensure the circulation of the rinsing liquid inside the circuit until a sufficient quantity of liquid has circulated.

According to a particular mode of the process for rinsing and filling the extracorporeal blood circuit by the device forming the object of the invention, the control unit 9 actuates the closing of the clamp 13 when the liquid reaches the level detector 8' in the arterial chamber 6', and acts on the distributor 14 to cause the venous chamber 6 to communicate with the pump 7 which is actuated to withdraw air from the chamber.

The action of pump 7 is maintained until the low pressure created inside the venous chamber 6 reaches a predetermined value corresponding to air pressure reduction conditions within the haemodialyser that are favorable to the proper degassing of the haemodialyser when being filled. When the pressure measured by the transducer 16 reaches the predetermined value, the control unit 9 again terminates the operation of pump 5. Liquid then fills the blood compartment of the haemodialyser 4, until it reaches the level detector 8. At this moment, the control unit 9 stops pump 7, opens the clamp 13, and sends a signal to the distributor 14 to cause the venous chamber 6 to communicate with the atmosphere for a very short time. Rinsing of the circuit then continues, through the operation of the pump 5.

It is possible to adjust the pressure inside each chamber 6 and 6' as follows. The data coming from the pressure transducers 16 and 16' are transmitted to the control unit 9 which can compare them with reference values or ranges of reference values. Based on this comparison, the control unit 9 sends a signal to the pump 7 and the distributor 14 to cause the quantity of air to vary inside the chambers to obtain the desired pressures.

When the circuit has been sufficiently rinsed, which can be directly determined by the control unit 9 using data coming from the balance 20, the clamps 12 and 13 are closed and the pump 5 is stopped. The arterial portion 1 of the extracorporeal circuit is then connected to a source of blood to be treated, such as a patient.

The pump 5 is then restarted and the clamps 12 and 13 are opened to cause the blood to circulate in the circuit, thereby forcing any remaining rinsing solution downstream until the present of blood is detected by a detector 19 located in the venous portion 2 downstream of the chamber 6. The clamps 12 and 13 are then closed and the venous portion 2 is connected to the patient.

After the clamps 12 and 13 have been opened, blood treatment by haemodialysis can actually start, irrespective of whether the extracorporeal blood circuit is used in the two needle mode or in the single needle mode. In the latter case, it is possible to use the pump 7 again to correct the pressure inside the chambers 6 and 6', if this proves necessary according to the data provided by the transducer 16 and 16'.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for treating blood including an extracorporeal blood circuit, the device comprising:

an arterial portion of the circuit for conveying liquid from a source to a treatment device in fluid communication with the arterial portion;

a venous portion of the circuit for conveying treated liquid away from the treatment device, the venous portion being in fluid communication with the treatment device;

at least one circulation pump in operative communication with the circuit;

an arterial chamber in fluid communication with the arterial portion of the circuit for containing liquid in a lower portion thereof, and for containing gas in an upper portion thereof;

a venous chamber in fluid communication with the venous portion of the circuit for containing liquid in a lower portion thereof, and for containing gas in an upper portion thereof;

a chamber pump operatively connected to at least one of the arterial and venous chambers for varying a quantity of gas inside at least one of the arterial and venous chambers;

means associated with at least one of the arterial and venous chambers for detecting a liquid level within at least one of the arterial and venous chambers and for outputting a corresponding signal;

means, communicating with the chamber pump and with the level detecting means, for controlling the chamber pump in response to the signal from the level detecting means in order to obtain a predetermined liquid level within at least one of the arterial and venous chambers, the controlling means including means for ensuring that predetermined high liquid levels are simultaneously reached in both the arterial and venous chambers, and means for ensuring that predetermined low liquid levels are simultaneously reached in both the arterial and venous chambers.

2. An apparatus according to claim 1 wherein said chamber pump is a gas pump.

3. An apparatus according to claim 1 wherein said controlling means includes means for determining a reference value for the signal of the level detecting means, the reference value corresponding to a predetermined optimum level of liquid in at least one of the arterial and venous chambers, determined reference value, means for checking whether the signal of the level detecting means falls within the determined reference range, and means for determining whether to add or withdraw air from at least one of the arterial and venous chambers so that the liquid in at least one of the arterial and venous chambers reaches a desired level.

4. An apparatus according to claim 1 wherein the controlling means includes a microprocessor.

5. An apparatus according to claim 1 further including means for selectively causing the chamber pump to communicate with the arterial chamber and the venous chamber.

6. An apparatus according to claim 1 wherein said level detecting means is capable of outputting signals corresponding to a high liquid level and a low liquid level.

7. An apparatus according to claim 6 wherein said level detecting means is a single sensor.

8. An apparatus according to claim 6 wherein the level detecting means includes at least one high level detector and at least one low level detector.

9. An apparatus according to claim 1 wherein the level detecting means is two sensors, one sensor corresponding to the arterial chamber and the other sensor corresponding to the venous chamber.

10. An apparatus according to claim 1 further including means associated with the at least one of the arterial and venous chambers for measuring the pressure inside at least one of the arterial and venous chambers and for communicating the measured pressure to the controlling means, the controlling means further including means for selecting a reference value for the pressure inside at least one of the arterial and venous chambers, means for determining a reference range encompassing the selected reference value, means for checking whether the value of the measured pressure falls within the reference range, means for determining whether to add or to withdraw gas from at least one of the arterial and venous chambers in order to obtain a desired pressure inside at least one of the arterial and venous chambers, and means for causing the chamber pump to vary the pressure within at least one of the arterial and venous chambers when a pressure measured within at least one of the arterial and venous chambers falls outside the reference range.

11. An apparatus according to claim 1 wherein the controlling means is also for controlling the chamber pump and the circulation pump in accordance with a predetermined program for automatically filling the extracorporeal blood circuit.

12. An apparatus according to claim 1, wherein the controlling means further includes:
   means for measuring a time period t necessary for the liquid level to change from the predetermined low liquid level to the predetermined high liquid level, or for the liquid level to change from the predetermined high liquid level to the predetermined low liquid level;
   means for determining a reference value for the time period t;
   means for comparing the measured time period t with the reference value; and
   means for sending a signal to the chamber pump to vary the quantity of gas inside at least one of the arterial and venous chambers in response to the comparing means.

13. A device for treating blood including an extracorporeal blood circuit, the device comprising:
   an arterial section of the circuit for conveying liquid from a source to a treatment device in fluid communication with the arterial section;
   a venous section of the circuit for conveying treated liquid away from the treatment device, the venous section being in fluid communication with the treatment device;
   a circulating pump in operative communication with the circuit;
   an arterial chamber in fluid communication with the arterial section of the circuit for containing liquid in a lower portion of the arterial chamber, and for containing gas in an upper portion of the arterial chamber;
   a venous chamber in fluid communication with the venous section of the circuit for containing liquid in a lower portion thereof, and for containing gas in an upper portion thereof;
   a chamber pump operatively connected to both the arterial and venous chambers for varying a quantity of gas inside the arterial and venous chambers;
   a first liquid level detector associated with the arterial chamber for detecting a liquid level within the arterial chamber and for outputting a signal corresponding to the liquid level detected;
   a second liquid level detector associated with the venous chamber for detecting a liquid level within the venous chamber and for outputting a signal corresponding to the liquid level detected; and
   a control unit, communicating with the chamber pump and the first and second liquid level detectors, for controlling the chamber pump in response to the signals from the first and second liquid level detectors to ensure that predetermined high liquid levels are simultaneously reached in both the arterial and venous chambers, and to ensure that predetermined low liquid levels are simultaneously reached in both the arterial and venous chambers.

* * * * *

UNITED STATES PATENT AND TRADEMARK OFFICE
CERTIFICATE OF CORRECTION

PATENT NO. : 5,382,227
DATED : January 17, 1995
INVENTOR(S) : Jean-Claude Riquier It is certified that error appears in the above-indentified patent and that said Letters Patent is hereby corrected as shown below:

Claim 3, column 8, line 56, before "determined", insert

--means for determining a reference range encompassing the--.

Claim 13, column 10, line 18, change "circulating" to --circulation--.

Signed and Sealed this

Twenty-first Day of March, 1995

Attest:

BRUCE LEHMAN

*Attesting Officer*          *Commissioner of Patents and Trademarks*